United States Patent [19]

Drewes et al.

[11] Patent Number: 5,439,874
[45] Date of Patent: Aug. 8, 1995

[54] HERBICIDAL SUBSTITUTED BICYCLO[3.1.0]HEXANES

[75] Inventors: Mark W. Drewes, Langenfeld; Rolf Kirsten, Monheim; Hans-Joachim Santel, Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 95,078

[22] Filed: Jul. 21, 1993

[30] Foreign Application Priority Data

Jul. 28, 1992 [DE] Germany .................. 42 24 928.7

[51] Int. Cl.⁶ ............... C07D 239/34; C07D 239/38; C07D 239/42; C07D 401/12; C07D 413/12; A01N 43/54
[52] U.S. Cl. ............... 504/239; 504/242; 504/243; 504/225; 504/196; 504/197; 544/300; 544/301; 544/302; 544/310; 544/311; 544/309; 544/312; 544/313; 544/122; 544/123; 544/243; 544/314; 544/316; 544/317; 544/318; 544/319; 544/320; 544/321; 544/324; 544/331; 544/332; 544/295; 544/296
[58] Field of Search ......... 504/242, 243, 239, 225; 544/300, 301, 302, 310, 311, 309, 312, 313, 314, 316, 317, 318, 319, 320, 321, 324, 331, 332, 296, 295

[56] References Cited

U.S. PATENT DOCUMENTS 4,973,354 11/1990 Hatanaka et al. .................. 544/299

FOREIGN PATENT DOCUMENTS 0431707  6/1991  European Pat. Off. .
0439243  7/1991  European Pat. Off. .

OTHER PUBLICATIONS

J. Org. Chem. (1990) 55-4144-4153 Padova et al.
J. Org. Chem. (1988) 53, 2984-2990 Taber et al.
J. Chem. Soc. Perkin Trans 1 (1986) pp. 1777-1780 Nemoto et al.
Tetrahedron Letters, vol. 22, No. 24, pp. 2297-2300, (1981) Morizawa et al.
Tetrahedron Letters, No. 45, pp. 3857-3860, (1976) Trost et al.
Chemical Abstracts, vol. 116, Mar. 30, 1992, No. 13, entry 128226j Kang et al.

*Primary Examiner*—John M. Ford
*Attorney, Agent, or Firm*—Sprung Horn Kramer & Wood

[57] ABSTRACT

The invention relates to novel substituted bicyclo[3.1.0-]hexanes of the formula

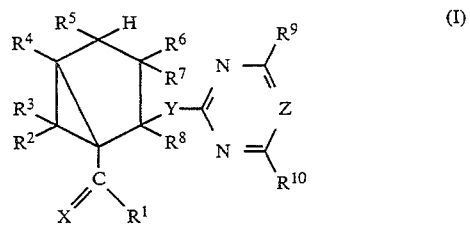

in which
$R^1$ represents, e. g., hydroxyl or alkoxy,
$R^2$ to $R^8$ represent, e. g., hydrogen or alkyl,
$R^9$ and $R^{10}$ represent, e.g., methyl or methoxy,
X represents, e.g., oxygen,
Y represents, e.g., oxygen or sulphur and
Z represents, e.g., CH or N, as well as salts of the free acid ($R^1$=OH) and their further functional derivatives, and furthermore to processes and novel intermediates for their preparation, and to their use as herbicides.

In addition, a novel process is described for preparing certain 2-keto-bicyclo[3.1.0]hexanes, which are required as intermediates, starting from correspondingly substituted $\alpha,\beta$-unsaturated carbonyl compounds (of the methacrolein type) and $\beta$-keto acid esters (of the acetoacetic acid ester type).

7 Claims, No Drawings

HERBICIDAL SUBSTITUTED BICYCLO[3.1.0]HEXANES

The invention relates to novel substituted bicyclo[3.1.0]hexanes, a process and new intermediates for their preparation and their use as herbicides.

Bicyclo[3.1.0]hexane derivatives have hitherto not attained any importance as herbicides.

Novel substituted bicyclo[3.1.0]hexanes of the general formula (I) have now been found

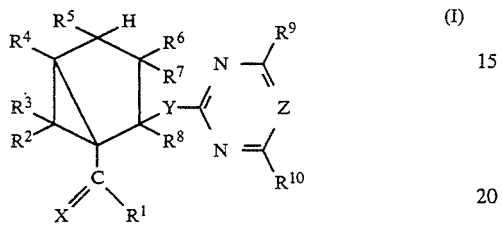

in which

R$^1$ represents hydrogen, hydroxyl, amino or a radical, which in each case may optionally be substituted, from the series alkyl, alkoxy, alkenyloxy, alkinyloxy, aryloxy, heteroaryloxy, alkylthio, arylthio, heteroarylthio, alkylamino, dialkylamino, alkylsulphonylamino, arylsulphonylamino or hydrazino, R$^2$ represents hydrogen, halogen, alkyl, alkoxy, aryl or alkoxycarbonyl, R$^3$ represents hydrogen or alkyl or - if R$^2$ denotes hydrogen, alkyl or halogen - also halogen, R$^4$ represents hydrogen, halogen, alkyl, aryl or alkoxycarbonylalkyl, R$^5$ represents hydrogen, alkyl or aryl, R$^6$ represents hydrogen, hydroxyl, amino, halogen, cyano, alkyl, alkoxy, aryl or alkoxycarbonyl, R$^7$ represents hydrogen or alkyl or - if R$^6$ denotes hydrogen, alkyl or halogen - also halogen, R$^8$ represents hydrogen, cyano, alkyl, aryl or alkoxycarbonylalkyl, R$^9$ and R$^{10}$ are identical or different and represent hydrogen, halogen or a radical, which in each case may optionally be substituted, from the series alkyl, alkoxy, alkylthio, alkylamino, dialkylamino, aryl or aryloxy, X represents oxygen or sulphur or - if R$^1$ denotes hydrogen or alkyl - also one of the following groupings:

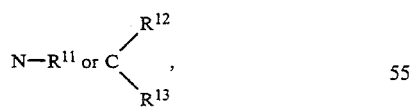

where

R$^{11}$ represents hydrogen, hydroxyl, amino or a radical, which in each case may optionally be substituted, from the series alkyl, alkenyl, alkinyl, alkoxy, alkenyloxy, alkoxycarbonylalkoxy, alkylamino, dialkylamino, alkylcarbonylamino, alkoxycarbonylamino, alkylsulphonylamino, aryl, aralkyl, aryloxy, aralkyloxy, arylamino, aralkylamino, N-alkyl-N-arylamino, hetarylamino, hetarylcarbonylamino, arylcarbonylamino or arylsulphonylamino, R$^{12}$ represents hydrogen, halogen, cyano, carboxyl, alkoxycarbonyl, alkylcarbonylamino or dialkoxyphosphoryl and R$^{13}$ represents formyl, cyano, carboxyl, hydroxymethyl, carbamoyl or a radical, which in each case may optionally be substituted, from the series alkoxycarbonyl, cycloalkyloxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl or phthalimidoxycarbonyl, or R$^{12}$ together with R$^{13}$, represents the grouping —CO—O—(CH$_2$)$_n$—, where n represents the numbers 1 to 4, Y represents oxygen, sulphur, imino (NH) or alkylimino (N-alkyl), and Z represents nitrogen or the group C-R$^{14}$, in which R$^{14}$ represents hydrogen, halogen, alkyl or alkoxy, as well as salts of the free acids (R$^1$=OH) and the anhydrides of the free acids.

The compounds of the formula (I) can exist in different isomeric forms (i.e. in different geometric and optical isomeric forms); all these isomers, which correspond to the general structural formula (I), are the subject of the invention.

It has furthermore been found that the novel bicyclo[3.1.0]hexanes of the general formula (I) are obtained if bicyclo[3.1.0]hexanes of the formula (II),

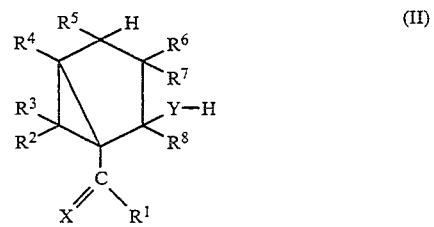

in which

R$^1$, R$^2$, R$^3$, R$^4$, R$^5$, R$^6$, R$^7$, R$^8$, X and Y have the meanings mentioned above in relation to formula (I), are reacted with azines of the formula (III),

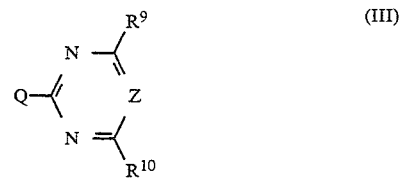

in which

R$^9$, R$^{10}$ and Z have the meanings mentioned above in relation to formula (I) and Q represents a nucleofugic leaving group, optionally in the presence of an acid acceptor and optionally in the presence of a diluent, and the free acids (R$^1$=OH) are optionally converted - by customary methods - into their salts or other functional derivatives.

The novel substituted bicyclo[3.1.0]hexanes of the formula (I) are distinguished by strong herbicidal activity.

The invention relates preferably to compounds of the formula (I) in which $R^1$ represents hydrogen, hydroxyl, amino or a radical, which in each case may optionally be substituted by halogen or $C_1$-$C_5$ -alkoxy, from the series $C_1$-$C_{5-1}$ -alkyl, $C_1$-$C_5$-alkoxy, $C_3$-$C_5$-alkenyloxy, $C_3$-$C_5$-alkinyloxy, cyano-$C_1$-$C_3$-alkoxy, methylthio-$C_1$-$C_3$-alkoxy, phenyloxy, pyridyloxy, (nitro)-quinolyloxy, isoquinolyloxy, $C_1$-$C_5$-alkylthio, phenylthio, pyrimidinylthio, $C_1$-$C_5$-alkylamino, ($C_1$-$C_2$-alkoxycarbonyl)-$C_1$-$C_5$-alkylamino, phenyl-($C_1$-$C_5$s-alkylamino), benzylamino, phenethylamino, di-($C_1$-$C_4$-alkyl)-amino, ($C_1$-$C_5$-alkyl)-sulphonylamino, ($C_6$-$C_{10}$-aryl)-sulphonylamino or a hydrazino radical, which may optionally be substituted by $C_1$-$C_2$-alkyl, $R^2$ represents hydrogen, halogen, $C_1$-$C_5$-alkyl, $C_1$-$C_5$-alkoxy, phenyl or ( $C_1$-$C_5$-alkoxy ) -carbonyl, $R^3$ represents hydrogen or $C_1$-$C_5$-alkyl or - if $R^2$ denotes hydrogen, alkyl or halogen - also halogen, $R^4$ represents hydrogen, halogen, $C_1$-$C_5$-alkyl or phenyl, $R^5$ represents hydrogen, $C_1$-$C_5$-alkyl or phenyl, $R^6$ represents hydrogen, hydroxyl, amino, halogen, cyano, $C_1$-$C_5$-alkyl, $C_1$-$C_5$-alkoxy, phenyl or ( $C_1$-$C_5$-alkoxy)-carbonyl, $R^7$ represents hydrogen or $C_1$-$C_5$-alkyl or - if $R^6$ denotes hydrogen, alkyl or halogen - also halogen, $R^8$ represents hydrogen, cyano, $C_1$-$C_5$-alkyl, phenyl or ($C_2$-$C_6$-alkoxycarbonyl ) -methyl, $R^9$ and $R^{10}$ are identical or different and represent hydrogen, halogen or a radical, which in each case may optionally be substituted by halogen or $C_1$-$C_3$-alkoxy, from the series $C_1$-$C_4$-alkyl, $C_1$-$C_4$-alkoxy, $C_1$-$C_4$-alkylthio, $C_1$-$C_4$-alkylamino, di- ($C_1$-$C_4$-alkyl )-amino, phenyl or phenoxy, X represents oxygen or sulphur or - if $R^1$ denotes hydrogen or alkyl - also one of the following groupings:

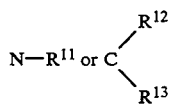

where $R^{11}$ represents hydrogen, hydroxyl, amino or a radical, which in each case may optionally be substituted by halogen, from the series $C_1$-$C_6$-alkyl, $C_3$-$C_b$ $_6$-alkenyl, $C_3$-$C_6$-alkinyl, $C_1$-$C_6$-alkoxy, $C_3$-$C_6$-alkenyloxy, $C_1$-$C_4$-alkoxy-carbonyl-$C_1$-$C_2$-alkoxy, $C_1$-$C_6$-alkylamino, di-($C_1$-$C_2$-alkyl) amino, $C_1$-$C_6$-alkylcarbonylamino, $C_1$-$C_6$-alkoxycarbonylamino, $C_1$-$C_6$-alkylsulphonylamino, or a radical, which in each case may optionally be substituted by nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkoxy-carbonyl and/or di-($C_1$-$C_2$-alkyl)-amino, from the series phenyl, phenyl-$C_1$-$C_4$-alkyl, phenoxy, phenyl-$C_1$-$C_4$-alkoxy, phenylamino, phenyl-$C_1$-$C_4$-alkylamino, N-($C_1$-$C_4$-alkyl ) -N-phenylamino, pyridylamino, pyrimidylamino, pyridylcarbonylamino, phenylcarbonylamino, furylcarbonylamino, thienylcarbonylamino or phenylsulphonylamino, $R^{12}$ represents hydrogen, halogen, cyano, carboxyl, $C_1$-$C_6$-alkoxycarbonyl, $C_1$-$C_6$-alkylcarbonylamino or di-($C_1$-$C_4$-alkoxy )-phosphoryl and $R^{13}$ represents formyl, cyano, carboxyl, hydroxymethyl, carbamoyl or a radical, which in each case may optionally be substituted by halogen, carboxyl or $C_1$-$C_4$-alkoxycarbonyl, from the series $C_1$-$C_6$-alkoxycarbonyl, $C_5$-$C_6$-cycloalkyloxycarbonyl, $C_1$-$C_6$-alkylthio-carbonyl, $C_1$-$C_6$-alkylaminocarbonyl, $C_5$-$C_6$-cycloalkylaminocarbonyl, di-($C_1$-$C_2$-alkyl)-aminocarbonyl, $C_1$-$C_4$-alkylaminocarbonyl-$C_1$-$C_4$-alkoxycarbonyl, di-($C_1$-$C_2$-alkyl)-aminocarbonyl-$C_1$-$C_4$-alkoxycarbonyl, phenylaminocarbonyl-$C_1$-$C_4$-alkoxycarbonyl, N-methyl-N-phenylaminocarbonyl-$C_1$-$C_4$-alkoxycarbonyl, or represents a radical, which in each case may optionally be substituted by methyl and/or ethyl, from the series pyrrolidinylcarbonyl, piperidinylcarbonyl, morpholinylcarbonyl or piperazinylcarbonyl, or represents a radical, which in each case may optionally be substituted by nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkoxy-carbonyl and/or di-($C_1$-$C_2$-alkyl-)amino, from the series phenoxycarbonyl, phenyl-$C_1$-$C_4$-alkoxycarbonyl, furylmethoxycarbonyl, thienylmethoxycarbonyl, phenylthiocarbonyl, phenyl-$C_1$-$C_4$-alkylthiocarbonyl, phenylaminocarbonyl, phenyl-$C_1$-$C_4$-alkylaminocarbonyl, N-($C_1$-$C_4$-alkyl)-N-phenylaminocarbonyl or phenylhydrazinocarbonyl, $C_1$-$C_4$-alkylhydrazinocarbonyl or phthalimidoxycarbonyl, or $R^{12}$ together with $R^{13}$ represents the grouping —CO—O—$(CH_2)_n$—, where n represents the numbers 1 to 4, Y represents oxygen, sulphur, imino (NH) or methylimino ($NCH_3$) and Z represents nitrogen or the grouping C-$R^{14}$, in which $R^{14}$ represents hydrogen, fluorine, chlorine, methyl or methoxy.

The invention further relates preferably to the sodium, potassium, magnesium, calcium, ammonium, $C_1$-$C_4$-alkylammonium, di-($C_1$-$C_4$-alkyl)-ammonium, tri-($C_1$-$C_4$-alkyl)ammonium, $C_5$- or $C_6$-cycloalkylammonium and di-($C_1$-$C_2$-alkyl)-benzyl-ammonium salts of compounds of the formula (I) in which $R^1$ represents OH and $R^2$ to $R^{14}$, X, Y and Z have the abovementioned preferred meanings.

Compounds which are particularly preferred according to the invention are those substituted bicyclo[3.1.0-]hexanes of the above formula (I) in which $R^1$ represents hydrogen, hydroxyl, amino or a radical, which in each case may optionally be substituted by fluorine, chlorine, methoxy or ethoxy, from the series methyl, ethyl, propyl, isopropyl, methoxy, ethoxy, propoxy, isopropoxy, cyanomethoxy, allyloxy, propargyloxy, methylthio-ethoxy, (nitro)-quinolyloxy, (fluoro)-phenylthio, (dimethoxy) pyrimidinylthio, methylamino, ethylamino, propylamino, isopropylamino, dimethylamino, diethylamino, methoxycarbonyl-methylamino, methoxycarbonylethylamino, (chloro)phenylethylamino, benzylamino, methylsulphonylamino, ethylsulphonylamino, phenylsulphonylamino or (dimethyl)-hydrazino, $R^2$ represents hydrogen, fluorine, chlorine, bromine, methyl, ethyl, propyl, isopropyl, phenyl, methoxycarbonyl or ethoxycarbonyl, $R^3$ represents hydrogen, methyl, ethyl, propyl or - if $R^2$ denotes hydrogen, alkyl or halogen- also fluorine, chlorine or bromine, $R^4$ represents hydrogen, fluorine, chlorine, bromine, methyl, ethyl, propyl, isopropyl or phenyl, $R^5$ represents hydrogen, methyl, ethyl, propyl, isopropyl or phenyl, $R^6$ represents hydrogen, chlorine, fluorine, methyl, ethyl, methoxy, ethoxy, phenyl, methoxycarbonyl or ethoxycarbonyl, $R^7$ represents hydrogen, methyl or ethyl or - if $R^6$ denotes hydrogen, alkyl or halogen - also chlorine or fluorine, $R^8$ represents hydrogen, cyano, methyl, ethyl, phenyl, methoxycarbonylmethyl or ethoxycarbonylmethyl, $R^9$ and $R^{10}$ are identical or different and represent hydrogen, chlorine, methyl, ethyl, trifluoromethyl, methoxymethyl, methoxy, ethoxy, difluoromethoxy, methylthio, methylamino, ethylamino, dimethylamino, phenyl or phenoxy, X represents oxygen or sulphur or - if $R^1$ denotes hydrogen or alkyl - also one of the following groupings

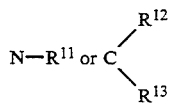

where $R^{11}$ represents hydrogen, hydroxyl, amino, methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenoxy, benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each of which may optionally be substituted by nitro, cyano, fluorine, chlorine, bromine, methyl, trifluoromethyl, methoxy, trifluoromethoxy, methylthio or trifluoromethylthio, $R^{12}$ represents hydrogen, fluorine, chlorine, cyano, carboxyl, $C_1$-$C_4$-alkoxycarbonyl, $C_1$-$C_4$-alkylcarbonylamino, dimethoxyphosphoryl or diethoxyphosphoryl and $R^{13}$ represents formyl, cyano, carboxyl, hydroxymethyl, carbamoyl, or a radical, which in each case may optionally be substituted by fluorine, chlorine, carboxyl or $C_1$-$C_4$-alkoxycarbonyl, from the series $C_1$-$C_4$-alkoxycarbonyl, $C_5$-$C_6$-cycloalkyloxycarbonyl, $C_1$-$C_4$-alkylthiocarbonyl, $C_1$-$C_4$-alkylaminocarbonyl, $C_5$-$C_6$-cycloalkylaminocarbonyl, dimethylaminocarbonyl, $C_1$-$C_4$-alkylaminocarbonyl-$C_1$-$C_4$-alkoxycarbonyl, dimethylaminocarbonyl-$C_1$-$C_4$-alkoxycarbonyl, N-methyl-N-Phenylamino-carbonyl-$C_1$-$C_4$-alkoxycarbonyl, or a radical, which in each case may optionally be substituted by methyl and/or ethyl, from the series pyrrolidinylcarbonyl, piperidinylcarbonyl, morpholinylcarbonyl or piperazinylcarbonyl, or represents a radical, which in each case may optionally be substituted by nitro, cyano, fluorine, chlorine, bromine, methyl, trifluoromethyl, methoxy, trifluoromethoxy, methylthio or trifluoromethylthio, from the series phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl, phenylhydrazinocarbonyl or phthalimidoxycarbonyl, or $R^{12}$, together with $R^{13}$, represents the groupings

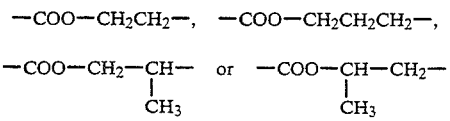

Y represents oxygen or imino ( NH ) and

Z represents nitrogen or a CH grouping.

A particularly interesting subgroup is formed by the compounds of the formula (I) in which $R^1$ represents hydroxyl, methoxy, ethoxy, propoxy, propargyloxy, cyanomethoxy, methylthioethoxy, methoxycarbonylmethylamino, methoxycarbonylethylamino, 4-chlorophenylethylamino, methylsulphonylamino, phenylsulphonylamino or 2,2-dimethylhydrazino, $R^2$ represents hydrogen, fluorine, chlorine, methyl or ethyl, $R^3$ represents hydrogen, methyl or ethyl, $R^4$ represents hydrogen, methyl, ethyl, propyl or isopropyl, $R^5$ represents hydrogen, methyl or ethyl, $R^6$ represents hydrogen, methyl or ethyl, $R^7$ represents hydrogen, methyl or ethyl, $R^8$ represents hydrogen or methyl, $R^9$ represents hydrogen, methyl or methoxy, $R^{10}$ represents methyl or methoxy, X represents oxygen, Y represents oxygen and Z represents nitrogen or the CH group, i.e. the free carboxylic acids ($R^1$=OH), certain esters and amides of these acids and their alkali metal salts, in particular the sodium and potassium salts.

The above-listed general radical definitions, or those listed in preference ranges, are valid both for the end products of the formula (I) and also, in a corresponding manner, for the starting compounds or intermediates which are required in each case for the preparation. These radical definitions can be combined at will among themselves, that is between the given preferred ranges as well.

The aliphatic hydrocarbon radicals (e.g. alkyl, alkenyl or alkinyl) listed in the definition of the compounds according to the invention are in each case straight-chain or branched, and this is also the case when they are in combination with heteroatoms (e.g. in alkoxy, alkylthio or alkylamino), or in an assemblage such as, for example, halogenoalkyl or halogenoalkoxy.

Halogen generally represents fluorine, chlorine, bromine or iodine, preferably fluorine, chlorine or bromine, in particular fluorine or chlorine.

If, for example, ethyl 2-hydroxy-5-methyl-bicyclo[3.1.0]-hexane-1-carboxylate and 2-chloro-4,6-dimethoxy-s-triazine are used as the starting compounds for the preparation process according to the invention, the course of the reaction can then be represented by the following formula diagram:

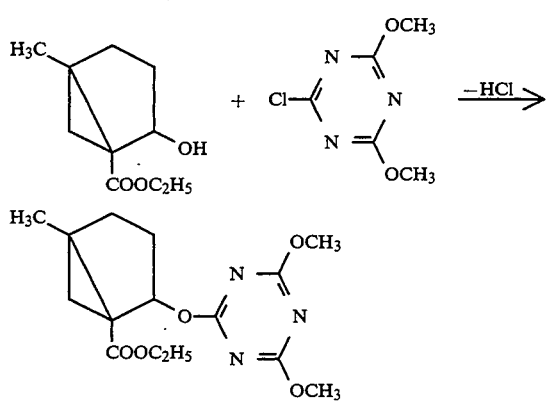

The bicyclo[3.1.0]hexanes which are to be used as starting compounds in the process according to the invention for preparing compounds of the formula (I) are generally defined by the above formula (II).

In formula (II), $R^1$ to $R^8$, X, Y and Z preferably or in particular have those meanings which have already been indicated above, in connection with the description of the compounds of the formula (I) according to the invention, as being preferred or particularly preferred for $R^1$ to $R^8$, X, Y and Z.

The bicyclo[3.1.0 ]hexanes of the formula (II) have not yet been described in the literature, but are novel and as such are also the subject of this invention.

The methods for preparing the compounds of the formula (II) are known in principle and depend in detail on the desired substituents:

(a) Thus, the compounds of formula (II), in which
$R^1$ has the meanings - except H, OH and alkyl - mentioned above in relation to formula (I),
$R^2$-$R^7$ have the abovementioned meanings,
$R^8$ represents H,
X represents O and
Y represents O,
(i.e. the esters, thioesters and amides) are obtained if the corresponding bicyclic ketones of the formula (IV)

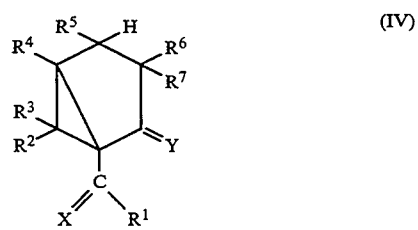

in which
$R^1$ to $R^7$, X and Y have the previously mentioned meanings,
are reduced at temperatures between 0° C. and 20° C. in a manner known per se using a complex metal hydride (such as, e.g. sodium borohydride [NaBH$_4$] or lithium aluminium hydride [LiAlH$_4$]) in a suitable solvent (e.g. an alcohol, such as methanol, ethanol, isopropanol or butanol, or an ether, such as, for example, diethyl ether or tetrahydrofuran).

(b) Compounds of the formula (I) , in which
$R^1$ to $R^7$, X and Y have the meanings mentioned at (a) and
$R^8$ represents alkyl or aryl,
can be prepared by reacting the bicyclic ketones of the formula (IV) in a manner known per se with suitable alkyl-metal compounds or aryl-metal compounds, e.g. with alkyl-lithium or aryl-lithium compounds (such as, for example, n-butyllithium or phenyllithium), or with the corresponding Grignard compounds.

(c) Compounds of the formula (II), in which
$R^1$ to $R^7$, X and Y have the meanings mentioned at (a) and
$R^8$ represents cyano or alkoxycarbonylalkyl,
can likewise be prepared in a manner known per se directly from the ketones (IV):
namely the cyanohydrins ($R^8$=CN) e.g. by reacting the ketones with hydrocyanic acid (HCN) or with a trialkylsilyl cyanide, e. g. trimethylsilyl cyanide [(CH$_3$)$_3$Si-CN], and subsequent partial hydrolysis,
and the ester derivatives ($R^8$=alkoxycarbonylethyl) by Reformatzki synthesis, i. e. reaction of the ketones with esters of halogeno fatty acids (such as, e.g. esters of bromoacetic acid) and zinc.

(d) Compounds of the formula (II) , in which
X represents

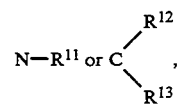

are obtained from the corresponding carbonyl compounds (X=O) in a manner known per se by reaction with amino or methylene compounds of the formula
H$_2$X, in which X represents

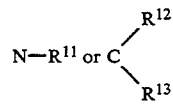

(cf. e..g. EP-A-451,653 $\triangleq$ U.S. Pat. No. 5,185,026 and EP-A-459,243 $\triangleq$ U.S. Pat. No. 5,167,693).

(e) Compounds of the formula (II), in which
X represents 0 and $R^1$ represents H (i.e. aldehydes ) , can be prepared in a conventional manner e.g. from the corresponding esters ($R^1$=alkoxy) by reduction to give the primary alcohols and oxidation thereof to give the aldehydes.

(f) Compounds of the formula (II), in which X represents S, can likewise be prepared in a conventional manner, either at the stage of the compounds (II) having X =O by O/S exchange or from precursors which already contain sulphur (see below).

(g) Compounds of the formula (II), in which Y represents S, can be prepared by analogous reduction from the corresponding bicyclic thioxo compounds of the formula (IV) having Y=S. The latter compounds are obtained in turn by O/S exchange, by reactions either of the ketones (IV) or of the β-keto esters (see below) to be used as starting compounds, with the so-called Lawesson reagent (cf. Bull. Soc. Chim. Belg. 1978, pages 223, 229, 299 and 525).

(h) Compounds of the formula (II), in which Y represents NH, can-be prepared from the corresponding ketones (IV) by reductive amination e. g. using sodium cyanoborohydride (Na [BH$_3$CN]) in the presence of ammonium acetate (cf. T. Sasaki, J. Chem. Soc., Perkin Trans. 1983, p. 3027 ).

(i) The N-alkyl compounds (II), having Y=N-alkyl, can be prepared from the amino compounds (II), having Y=NH, which are obtainable according to (h), by subsequent alkylation, e.g. using alkyl halides or sulphates in the presence of butyllithium/lithium diisopropylamide.

(j) Compounds of the formula (II) , in which
X represents O and R$^1$ represents alkyl (i.e. alkyl ketones) ,
can likewise be prepared in a conventional manner, e.g. from the corresponding acids (R$^1$=OH) by reductive alkylation using 2 molar equivalents of alkyllithium per mol of acid in the presence of an ether, such as, e.g., diethyl ether (cf., e.g., Organic Reactions Vol. 18 (1970), pages 1 to 97).

(k) compounds of the formula (II), in which
X represents O and R$^1$ represents OH (i.e. the free acids) , are most readily prepared by hydrolysis, under the usual conditions, of the corresponding esters (R$^1$=alkoxy, aryloxy, etc.) which have previously been obtained.

The bicyclic ketones of the formula (IVa),

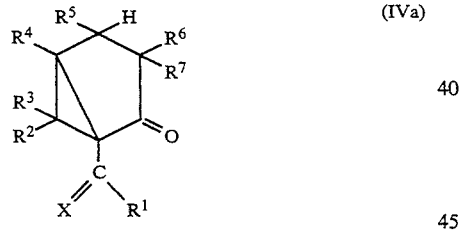

in which
R$^1$ to R$^7$ and X have the meanings mentioned above at (a), with the exception of the three following compounds: methyl 2-keto-6,6-dimethyl-bicyclo[3.1.0]hexane-1-carboxylate (cf. J. Org. Chem. 48, pp. 2076 to 2084 (1983)); as well as ethyl 2-keto-6-methyl-bicyclo[3.1.0]hexane-1-carboxylate and ethyl 2-keto-6-n-propyl-bicyclo[3.1.0]-hexane-1-carboxylate (cf. Bull. Chem. Soc. Japan 54, pp. 2154-2160 (1980)), are novel. The novel compounds of the formula (IVa) are likewise the subject of the present invention.

It has been found, surprisingly, that the bicyclic ketones of formula (IV), in which
R$^1$ represents alkoxy,
R$^4$ with the exception of hydrogen, has the abovementioned meanings, the radicals
R$^2$, R$^3$, R$^5$, R$^6$ and R$^7$ have the abovementioned meanings and
X represents oxygen,
can be prepared according to a novel inventive process which is characterised in that - according to the following reaction scheme -

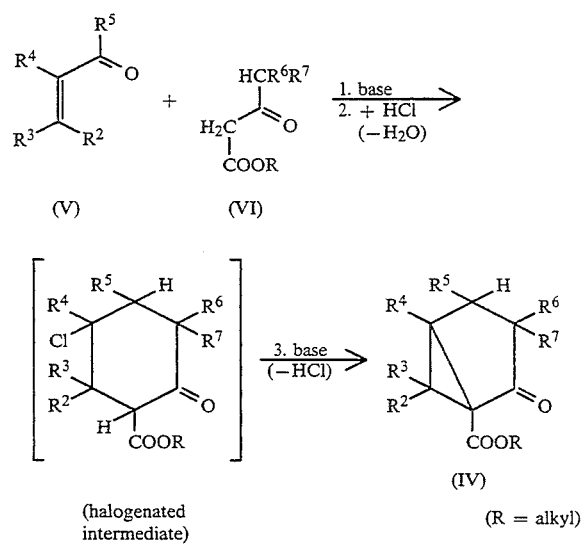

(α) an α, β-unsaturated carbonyl compound of the formula (V) is reacted with a β-keto ester of the formula (VI), where, in the formulae (V) and (VI),
R$^1$ represents alkoxy,
R$^4$ with the exception of hydrogen, has the abovementioned meanings, the radicals
R$^2$, R$^3$, R$^5$, R$^6$ and R$^7$ have the abovementioned meanings and
X represents oxygen,
in approximately equimolar quantities initially in the presence of a strong base [such as, e.g., NaH, NaNH$_2$, LiNCH(CH$_3$)$_2$ or an alcoholate, such as, e.g. NaOCH$_3$, NaOC$_2$H$_5$ or KOC(CH$_3$)$_3$] and in the presence of a polar solvent (e.g..ethanol, methanol, tetrahydrofuran, dimethyl sulphoxide, acetonitrile, dioxane or dimethylformamide; preferably ethanol) at temperatures of between −50° C. and +100° C., preferably of between −4020 C. and +80° C., particularly preferably of between 0° C. and +40° C., (β) the reaction product is subsequently - without intervening isolation - reacted at about 0° C. with anhydrous hydrogen chloride ( by saturating the solution with HC gas ) and (Y) finally, the halogenated intermediate thus formed is isolated, e. g. by distillation, and the latter is reacted again with a base (selected e.g. from the acid acceptors listed below in connection with the main process for preparing the end products (I); particularly preferably with 1,5-diazabicyclo[5.4.0]undec-5-ene (DBN), which can also serve as diluent) at temperatures of between 0° C. and 150° C., preferably of between 20° C. and 120° C., particularly preferably of between 50° C. and 100° C. with the formation of the three-membered ring, and thus of the bicyclo[3.1.0-]hexane skeleton, taking place with the elimination of hydrogen halide.

This novel process for preparing the bicyclic keto esters is surprising, and as such inventive, because, according to the state of the art (cf. F. M. Hauser et al., SYNTHESIS 1980, pp. 814–815), it was to be expected, in this reaction, that the cyclohexenone esters (A), which are isomeric with (IV), would be formed:

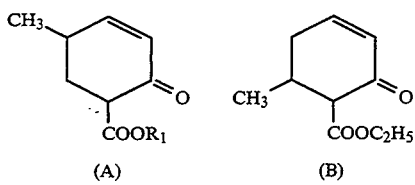

(A) (B)

The (A) compounds were the original goal of the synthesis, since, according F. M. Hauser et al. (loc. cit.), the comparable reaction of crotonaldehyde with ethyl acetoacetate leads to the cyclohexenone ester (B).

If methacrolein is used as the starting compound of the formula (V) and methyl acetoacetate as the starting compound of the formula (VI), the process for-preparing the bicyclic keto esters (IV) can then be illustrated by 5 the following formula diagram:

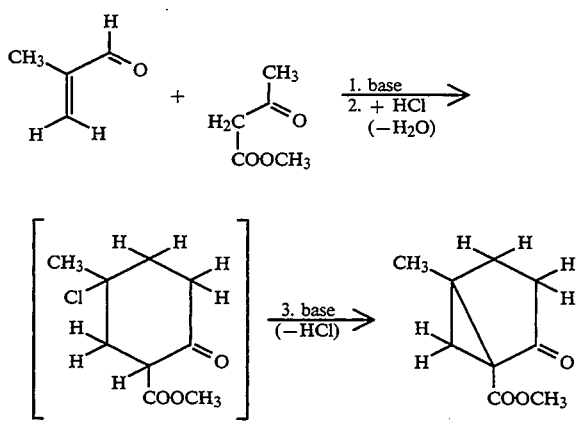

Bicyclic keto esters of the above formula (IV), in which

R$^1$ represents alkyl,

R$^4$ represents hydrogen,

R$^2$ to R$^7$ have the abovementioned meanings and

X represents oxygen, can be prepared according to methods known from the literature (cf. the references which have already been cited above J. Org. Chem. 48, pp. 2076–2084 (1983) and Bull. Chem. Soc. Japan Vol.54, pp. 2154–2160 (1981)).

The bicyclo[3.1.0]hexane ring skeleton having different substituents, which is characteristic of the intermediates of the type (IV) and (II), can also be synthesised by further previously known methods; the substituents can be introduced either by selecting suitable starting compounds or, optionally, by subsequent conversion using conventional methods. Carbene addition and methylene transfer to suitable cyclopentene derivatives may be mentioned as exemplifying this.

Thus, e.g. according to the process of E. J. Corey et al., the methylene group (—CH$_2$—) can be added specifically to the conjugated C=C double bond of a cyclopentenonecarboxylic acid ester of the type (C), with the formation of a cyclopropane ring, by reacting, for example, according to the following reaction scheme:

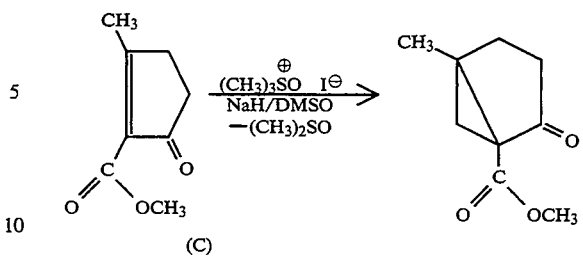

(C)

methyl 2-keto-5-methyl-cyclopentenyl-l-carboxylate (C) with dimethyloxosulphonium methylide [(CH$_3$)$_2$S$^\oplus$$^{O-C}$$^\ominus$H$_2$]- produced from trimethyloxosulphonium iodide [(CH$_3$)$_3$S$^\oplus$OI$^\ominus$] by deprotonating using strong bases such as sodium hydride (NaH) in dimethyl sulphoxide (DMSO) or tetrahydrofuran (THF) - (cf. E. J. Corey and M. Chaykovsky, J. Amer. Chem. Soc. Vol.87 (1965), pages 1353 to 1364).

The bicyclic keto esters of the above formula (IV), in which R$^1$ has the rest of the abovementioned meanings (i.e. the free acids, the aldehydes and ketones, and additionally unsaturated, aromatic and heteroaromatic esters, thioesters and amides), can be obtained by conventional processes from the previously prepared alkyl esters (R$^1$=alkoxy); these conventional processes for converting the functional groups (—C(X)R$^1$) have already been listed above in connection with the intermediates of the formula (II).

In summary, it can be emphasised, with regard to the synthesis of the intermediates of the formulae (II) and (IV), that only the synthesis of the bicyclo[3.1.0]hexane system by the above-described novel condensation and addition/elimination reaction is inventive, and that all subsequent modifications of the basic structure (IV) or (II) are possible using methods which are known in principle. The relevant reaction conditions (e.g. selection of the suitable solvents, auxiliary substances, quantity ratios and ranges of temperature and pressure) can readily be determined within the scope of the customary procedures.

The azines which are additionally to be used as starting compounds in the process according to the invention for preparing the bicyclo[3.1.0]hexanes of the formula (I) are defined by formula (III). In formula (IIi), R$^9$, R$^{10}$ and Z preferably or in particular have those meanings which have already been indicated above, in connection with the description of the compounds of the formula (I) according to the invention, as being preferred or as being particularly preferred for R$^9$, R$^{10}$ and Z; additionally, in formula (III), Q preferably represents fluorine, chlorine, bromine or C$_1$-C$_4$-alkylsulphonyl, in particular chlorine or methylsulphonyl.

Examples of the starting compounds of the formula (III) which may be mentioned are:

2-chloro-4,6-dimethyl-pyrimidine, 2-chloro-4-methyl-6-methoxy-pyrimidine, 2-chloro-4,6-dimethoxypyrimidine, 2-chloro-4-methylpyrimidine, 2-chloro-4,6-dimethyl-s-triazine, 2-chloro-4-methoxy-6-methyl-s-triazine, 2-chloro-4,6-dimethoxy-s-triazine, as well as 2-methylsulphonyl-4,6-dimethyl-pyrimidine, 2-methylsulphonyl-4,6-dimethoxy-pyrimidine and 2-methylsulphonyl-4-methylpyrimidine.

The azines of the formula (III) are known and/or can be prepared by processes which are known per se (cf. J.

Chem. (1957), p. 1830, p. 1833; J. Org. Chem. 26 (1961), p. 792; U.S. Pat. No. 3,308,119; U.S. Pat. No. 4,711,959).

The process according to the invention for preparing the novel compounds of the formula (I) is preferably carried out using diluents. Suitable diluents for this purpose are inert organic solvents. Among these are, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone as well as dimethyl sulphoxide, tetramethylene sulphone and hexamethylphosphoric triamide.

All acid-binding agents customarily used for reactions of this nature may be employed as acid acceptors in the process according to the invention. Those which are preferred are alkali metal hydroxides, such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, and sodiumand potassium tert-butylate, and in addition aliphatic, aromatic or heterocyclic amines, for example triethylamine, trimethylamine, dimethylaniline, dimethylbenzylamine, pyridine, 1,5-diazabicyclo[4.3.0]-non-5-ene (DBN), 1,8-diazabicyclo[5.4.0]-undec-7-ene (DBU) and 1,4-diazabicyclo[2.2.2]-octane (DABCO).

In the process according to the invention, the reaction temperatures may be varied over a relatively wide range. In general, temperatures of between 0° C. and 150° C., preferably temperatures of between 10° C. and 100° C., are employed.

The process according to the invention is generally carried out under atmospheric pressure. However, it is also possible to operate under elevated or reduced pressure.

The starting materials required in each case to carry out the process according to the invention are generally employed in quantities which approach equimolar. However, it is also possible to use one of the two components employed on each occasion in a relatively large excess. The reactions are generally carried out in a suitable diluent in the presence of an acid acceptor, and the reaction mixture is stirred for several hours at the temperature required on each occasion. In the process according to the invention, working up takes place on each occasion according to customary methods (compare the preparation examples).

The active compounds of the formula (I) according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are suitable for combating monocotyledon and dicotyledon weeds, in particular in dicotyledon cultures, both in the pre-emergence and in the post-emergence process.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryl-oxy-phenoxy-alkanoic esters such as, for example, diclofog-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor. and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixture with other known active compounds, such as fungicides, insecticides, acaricides, nematocides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

Preparation examples:

Example 1

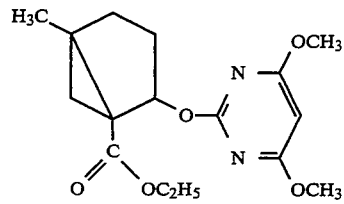

A mixture of 1.4 g (6.5 mmol) of 4,6-dimethoxy-2-methyl-sulphonyl-pyrimidine, 1.2 g (6.5 mmol) of ethyl 2-hydroxy-5-methyl-bicyclo-[3.1.0]-hexane-1-carboxylate, 1.1 g (5.5 mmol) of potassium carbonate and 20 ml of acetonitrile is heated under reflux for 12 hours and subsequently concentrated. The residue is extracted with water/ethyl acetate with shaking and the organic phase is separated off, dried with sodium sulphate and filtered. The solvent is distilled off from the filtrate under water pump vacuum.

1.1 g (52% of theory) of ethyl 2-(4,6-dimethoxy-pyrimidin-2-yloxy)-5-methyl-bicyclo [3.1.0 ] hexane-1-carboxylate are obtained in the form of an oil.

$^1$H-NMR spectrum (300 MHz; tetramethylsilane as internal standard=TMS ): δ=3.85 ppm (s,2 methoxy groups).

The same measurement conditions (300 MHz; TMS) apply for all the NMR data given subsequently.

Example 2

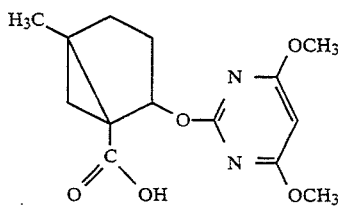

2-(4,6-Dimethoxy-pyrimidin-2-yloxy)-5-methyl-bicyclo-[3.1.0]hexane-1-carboxylic acid with a melting point of 186° C., prepared by ester hydrolysis of the corresponding ethyl ester (Example 1) under customary conditions.

Example 3

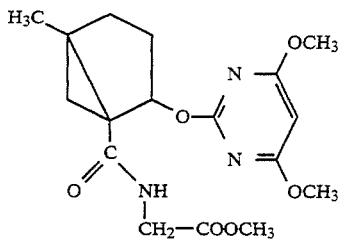

1 g (3.4 mmol) of 2-(4,6-dimethoxy-pyrimidin-2-yloxy)-5-methyl-bicyclo[3.1.0]hexane-1-carboxylic acid is dissolved in 50 ml of dichloromethane and mixed with 2.1 g of triethylamine. 0.53 g (3.4 mmol) of phosphorus oxychloride, dissolved in 5 ml of dichloromethane, is added dropwise at −5° C. and the mixture is subsequently stirred for 5 minutes. A solution of 0.9 g (7.1 mmol) of methyl aminoacetate (glycine methyl ester) in 5 ml of dichloromethane is then added, with continued stirring, to the solution of the acid chloride. The reaction mixture is then allowed to reach room temperature within the space of 15 minutes. Subsequently, the organic phase is separated off, washed three times with water, dried over magnesium sulphate and evaporated. The remaining residue is purified by means of (flash) chromatography. 2-(4,6-Dimethoxy-pyrimidin-2-yloxy)-5-methyl-bicyclo-[3.1.0]hexane-1-carboxylic acid N-(methoxycarbonyl-methyl)-amide is obtained in the form of an oil.

$^1$H-NMR spectrum:
δ=3.58 ppm (s; —COOCH$_3$).

Example 4

Sodium 2-(4,6-dimethoxy-pyrimidin-2-yloxy)-5-methylbicyclo [3.1.0]hexane-1 -carboxylate with a melting point of 125 ° C. decomp.=with decomposition), prepared by neutralisation of the carboxylic acid (Example 2) under the usual conditions.

Example 5

Potassium 2- ( 4,6-dimethoxy-pyrimidin-2-yloxy ) -5-methylbicyclo[3.1.0 ]hexane-1-carboxylate with a melting point of 165° C. (decomp.), prepared in an analogous manner to Example 4.

Example 6

Methyl 2-(4,6-dimethoxy-pyrimidin-2-yloxy ) -5-methyl-bicyclo[ 3.1.0 ]hexane-1-carboxylate with a melting point of 76° C. prepared in an analogous manner to Example 1.

Example 7 n-Propyl 2-(4,6-dimethoxy-pyrimidin-2-yloxy)-5-methyl-bicyclo[3.1.0]hexane-1-carboxylate in the form of an oil, prepared in an analogous manner to Example 1.

$^1$H-NMR spectrum:
δ=0.86 ppm (t; —COOCH$_2$CH$_2$CH$_3$) .

Example 8

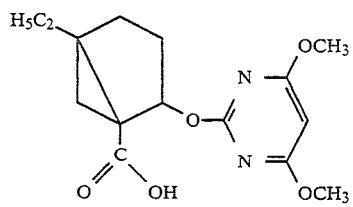

2-(4,6-Dimethoxy-pyrimidin-2-yloxy) -5-ethyl-bicyclo-[3.1.0 ]hexane-1-carboxylic acid in the form of an oil, prepared in an analogous manner to Examples 1 and 2.

$^1$H-NMR spectrum:
δ=3.85 ppm (s; 2 OCH$_3$).

Example 9

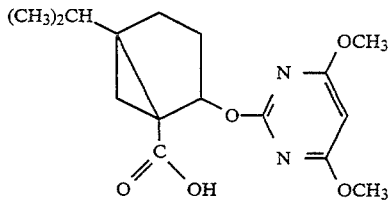

2-(4,6-Dimethoxy-pyrimidin-2-yloxy ) -5-isopropyl-bicyclo-[3.1.0 ]hexane-1-carboxylic acid with a melting point of 170° C. prepared in an analogous manner to Examples 1 and 2.

Example 10

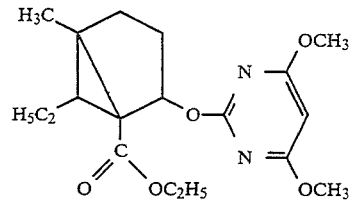

Ethyl 2-(4,6-dimethoxy-pyrimidin-2-yloxy)-5-methyl-6-ethyl-bicyclo[3.1.0]hexane-1-carboxylate as an isomeric mixture) in the form of an oil, prepared in an analogous manner to Example 1.

$^1$H-NMR spectrum:
δ=6.12 (t;

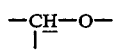

in the 2-position).

Example 11

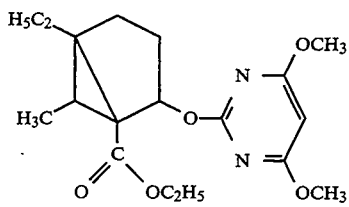

Ethyl 2-(4,6-dimethoxy-pyrimidin-2-yloxy)-5-ethyl-6-methyl-bicyclo[3.1.0]hexane-1-carboxylate ( as an isomer mixture) in the form of an oil, prepared in an analogous manner to Example 1.

$^1$H-NMR spectrum:

δ=6.10 ppm (t;

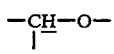

in the 2- position).

Example 12

2-(4,6-Dimethoxy-pyrimidin-2-yloxy) -5-ethyl-6-methyl-bicyclo-[3.1.0 ]hexane-1-carboxylic acid ( as an isomer mixture) in the form of an oil, prepared by ester hydrolysis of the corresponding ethyl ester (Example 11) under customary conditions.

$^1$H-NMR spectrum:

δ=5.98 ppm (t;

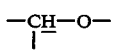

in the 2-position).

Example 13

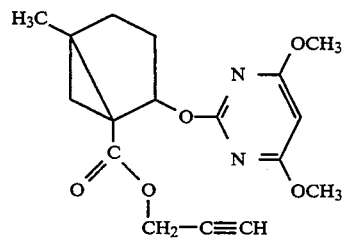

Propargyl 2-(4,6-dimethoxy-pyrimidin-2-yloxy ) -5-methyl-bicyclo[3.1.0]hexane-1-carboxylate with a melting point of 170° C., prepared in an analogous manner to Example 3 via the acid chloride.

Example 14

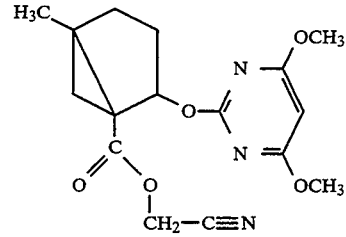

Cyanomethyl 2-(4,6-dimethoxy-pyrimidin-2-yloxy ) -5-methyl-bicyclo[3.1.0]hexane-1-carboxylate in the form of an oil, prepared by reacting the sodium salt of the carboxylic acid (Example 4) with commercially available chloroacetonitrile.

$^1$H-NMR spectrum:

δ=4.68 and 4.80 ppm.(AB system; —COO—CH$_2$—CN).

Example 15

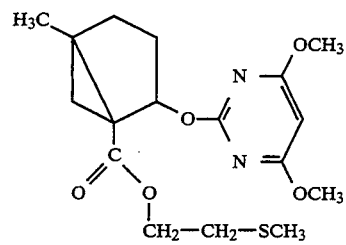

2-Methylthioethyl 2-(4,6-dimethoxy-pyrimidin-2-yloxy) -5-methyl-bicyclo[3.1.0 ]hexane-1-carboxylate in the form of an oil, prepared in an analogous manner to Example 3.

$^1$H-NMR spectrum:

δ=2.09 ppm (s; —CH$_2$CH$_2$—SCH$_3$).

Example 16

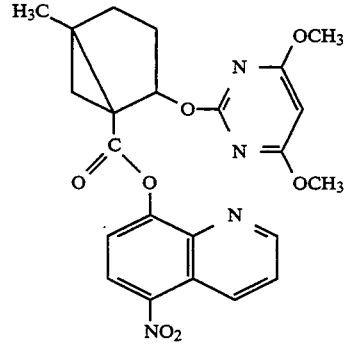

5-Nitro-8-quinolyl 2-(4,6-dimethoxy-pyrimidin-2-yloxy) -5-methyl-bicyclo[3.1.0]hexane-1-carboxylate in the form of an oil, prepared in an analogous manner to Example 3.

$^1$H-NMR spectrum: δ=3.83 ppm (s; 2 —OCH$_3$).

Example 17

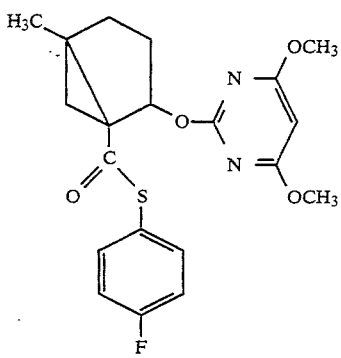

S-(4-Fluorophenyl) 2-(4,6-dimethoxy-pyrimidin-2-yloxy)-5-methyl-bicyclo [3.1.0]hexane-1-thiocarboxylate with a melting point of 89°20 C., prepared in an analogous manner to Example 3.

Example 18

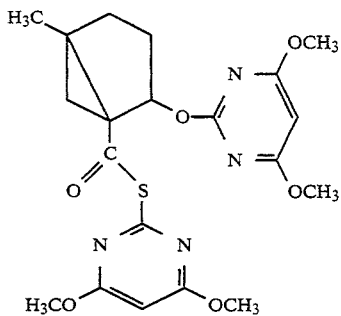

S-(4,6-Dimethoxy-pyrimidin-2-yl) 2-(4,6-dimethoxy-pyrimidin-2-yloxy)-5-methyl-bicyclo[3.1.0]hexane-1-thiocarboxylate with a melting point of 146° C., prepared in an analogous manner to Example 3.

Example 19

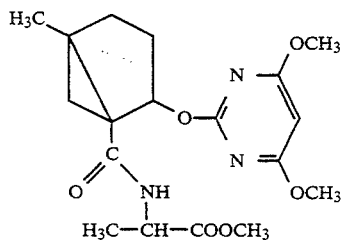

2-(4,6-Dimethoxy-pyrimidin-2-yloxy)-5-methyl-bicyclo-[3.1.0]hexane-1-carboxylic acid N-(1-methoxycarbonyl-ethyl)-amide in the form of an oil, prepared in analogous manner to Example 3.

$^1$H-NMR spectrum:
$\delta = 3.93$ ppm (s; 2—OCH$_3$).

Example 20

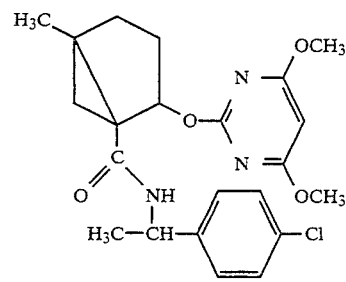

2-(4,6-Dimethoxy-pyrimidin-2-yloxy)-5-methyl-bicyclo-[3.1.0]hexane-1-carboxylic acid N-[1-(4-chlorophenyl)-ethyl]-amide in the form of an oil, prepared in an analogous manner to Example 3.

$^1$H-NMR spectrum:
$\delta = 3.85$ ppm (s; 2OCH$_3$).

Example 21

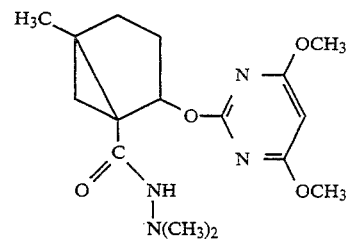

2-(4,6-Dimethoxy-pyrimidin-2-yloxy)-5-methyl-bicyclo-[3.1.0]hexane-1-carboxylic acid (2,2-dimethyl)-hydrazide with a melting point of 78° C., prepared in an analogous manner to Example 3.

Example 22

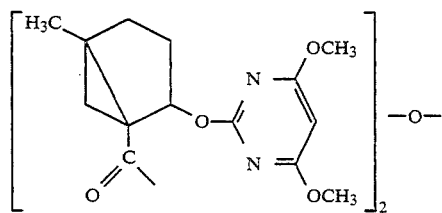

2-(4,6-Dimethoxy-pyrimidin-2-yloxy)-5-methyl-bicyclo-[3.1.0]hexane-1-carboxylic anhydride with a melting point of 66° C., prepared by reacting the sodium salt of the carboxylic acid (Example 4) with the corresponding acid chloride.

Preparation of the starting compounds

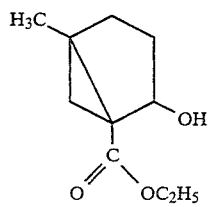

0.4 g (0.01 mol) of sodium borohydride is added at room temperature to 1.8 g (0.01 mol) of ethyl 2-keto-5-methyl-bicyclo[3.1.0]hexane-1-carboxylate, dissolved in 20 ml of ethanol, and the mixture is then subsequently stirred at room temperature for about 12 hours. The reaction mixture is poured into water. The residue is extracted with diethyl ether, concentration is effected, and the crude product is chromatographed on silica gel with hexane/ethyl acetate as eluent. 1.5 g (82% of theory) of ethyl 2-hydroxy-5-methyl-bicyclo[3.1.0]hexane-1-carboxylate are obtained in the form of an oil.

¹H-NMR spectrum

δ = 1.12 ppm (s, tert. methyl group, in the 5 position)

The following intermediates of the formula (II) can be prepared in an analogous manner:

| | ¹H-NMR spectrum: |
|---|---|
| Example II-2 (structure with $H_5C_2$, OH, $O=C-OCH_3$) | δ = 4.92 ppm (t; —C$\underline{H}$—OH in the 2-position) |
| Example II-3 (structure with $(CH_3)_2CH$, OH, $O=C-OCH_3$) | δ = 4.91 ppm (t; —C$\underline{H}$—OH in the 2-position) |
| Example II-4 (structure with $H_3C$, $H_5C_2$, OH, $O=C-OC_2H_5$) | δ = 4.76 ppm (t; —C$\underline{H}$—OH in the 2-position) |
| Example II-5 (structure with $H_5C_2$, $H_3C$, OH, $O=C-OC_2H_5$) | δ = 4.77 ppm (t; —C$\underline{H}$—OH in the 2-position) |
| Example IV-1 (structure with $H_3C$, =O, $O=C-OC_2H_5$) | |

74 g (0.57 mol) of ethyl acetoacetate are added to a solution of 0.5 g of sodium in 100 ml of dried ethanol, 40 g (0.57 mol) of methacrolein are added dropwise and the mixture is stirred at room temperature for about 12 hours. The mixture is then saturated at 0° C. with dry HCl gas and subsequently stirred at room temperature for about 48 hours. The solvent is removed and the remaining residue is distilled in vacuo. The fractions passing over at from 95° C. to 105°C./0.013 mbar are combined. 32.3 g are obtained of a yellow oil, which is,-dissolved in 50 ml of 1,5-diazabicyclo[5.4.0]undec-5-ene,-heated to 80°C., and the solution is stirred for a further 30 minutes at this temperature. The solution thus obtained is poured into water, extracted with methylene chloride and subsequently washed with 10% hydrochloric acid, dried over sodium sulphate and concentrated.

20.4 g of ethyl 2-keto-5-methyl-bicyclo[3.1.0]hexane-1-carboxylate are obtained in the form of an oil.

1H-NMR spectrum:

δ = 1.37 ppm (s; tert. methyl group, in the 5 position)

The following intermediates of the formula (IV) can be prepared in an analogous manner:

| | ¹H-NMR spectrum: |
|---|---|
| Example IV-2 (structure with $H_5C_2$, =O, $O=C-OCH_3$) | δ = 1.46 ppm and 1.98 ppm (AB-system; —C$\underline{H}_2$— in the 6-position) |
| Example IV-3 (structure with $(CH_3)_2CH$, =O, $O=C-OCH_3$) | δ = 1.47 ppm and 1.98 ppm (AB-system; —C$\underline{H}_2$— in the 6-position) |
| Example IV-4 (structure with $H_3C$, $H_5C_2$, =O, $O=C-OC_2H_5$) | δ = 1.41 ppm (s; tert. methyl group in the 5-position) |
| Example IV-5 (structure with $H_5C_2$, $H_3C$, =O, $O=C-OC_2H_5$) | δ = 1.30 ppm (d; methyl group in the 6-position) |

Application examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compound 2, for example, shows a strong herbicidal activity. Thus, using a quantity of 500 g/ha, the weeds Alopecurus, Bromus, Cyperus, Echinochloa, Veronica and Viola, for example, are 90 to 100% destroyed, while at the same time the compound is well tolerated by cultivated plants, such as, for example, soya bean.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5 –15 cm are sprayed with the preparation of the active compound in such a way as to apply the particular amounts of active compound desired per unit area. After three weeks, the degree of damage to the plants is rated in % damage in comparison to the development of the untreated control.

The figures denote:
0% = no action (like untreated control)
100% = total destruction In this test also, the compound 2, for example, shows a strong herbicidal activity. Thus, using a quantity of 500 g/ha, the weeds Bromus, Sorghum, Abutilon, Amaranthus, Sinapis and Veronica, for example, are 90 to 100% destroyed, while at the same time the compound is fully tolerated by cultivated plants, such as, for example, soya bean.

It will be appreciated that the instant specification and claims are set forth by way of illustration and not limitation, and that various modifications and changes may be made without departing from the spirit and scope of the present invention.

We claim:

1. A substituted bicyclo[3.1.0]hexane of the formula (I)

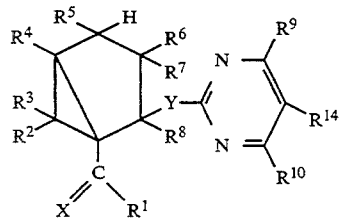

in which $R^1$ is hydrogen, hydroxyl, amino or a radical (optionally substituted by halogen or $C_1$–$C_5$-alkoxy) selected from the group consisting of $C_1$–$C_5$-alkyl, $C_1$–$C_5$-alkoxy, $C_3$–$C_5$-alkenyloxy, $C_3$–$C_5$-alkinyloxy, cyano-$C_1$–$C_3$-alkoxy, methylthio-$C_1$–$C_3$-alkoxy, phenyloxy, pyridyloxy, (nitro)-quinolyloxy, isoquinolyloxy, $C_1$–$C_5$-alkylthio, phenylthio, pyrimidinylthio, $C_l$–$C_5$-alkylamino, ($C_1$–$C_2$-alkoxycarbonyl)-$C_1$–$C_5$-alkyl-amino, phenyl-($C_1$–$C_5$-alkylamino), benzylamino, phenethylamino, di-($C_1$–$C_4$-alkyl) amino, ($C_1$–$C_5$-alkyl)-sulphonylamino, ($C_6$–$C_{10}$-aryl)-sulphonylamino and a hydrazino radical optionally be substituted by $C_1$–$C_2$-alkyl, $R^2$ is hydrogen, halogen, $C_1$–$C_5$-alkyl, $C_1$–$C_5$-alkoxy, phenyl or ($C_1$–$C_5$-alkoxy)-carbonyl, $R^3$ is hydrogen or $C_1$–$C_5$-alkyl or - if $R^2$ is hydrogen, alkyl or halogen - also may be halogen, $R^4$ is hydrogen, halogen, $C_1$–$C_5$-alkyl or phenyl, '$R^5$ is hydrogen, $C_1$–$C_5$-alkyl or phenyl, $R^6$ is hydrogen, hydroxyl, amino, halogen, cyano, $C_1$–$C_5$-alkyl, $C_1$–$C_5$-alkoxy, phenyl or ($C_1$–$C_5$-alkoxy)-carbonyl, $R^7$ is hydrogen or $C_1$–$C_5$-alkyl or - if $R^6$ is hydrogen, alkyl or halogen,- also may be halogen, $R^8$ is hydrogen, cyano, $C_1$–$C_5$-alkyl, phenyl or -($C_2$–$C_6$-alkoxycarbonyl-methyl, $R^9$ and $R^{10}$ each independently is hydrogen, halogen or a radical (optionally substituted by halogen or $C_1$–$C_3$-alkoxy), selected from the group consisting of $C_1$–$C_4$-alkyl, $C_1$–$C_4$-alkoxy, $C_1$–$C_4$-alkylthio, $C_1$–$C_4$-alkylamino, di-($C_1$–$C_4$-alkyl)-amino, phenyl and phenoxy, X is oxygen or sulphur or - if $R^1$ is hydrogen or alkyl - also may be:

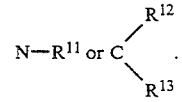

where $R^{11}$ is hydrogen, hydroxyl, amino or a radical (optionally substituted by halogen) selected from the group consisting of $C_1$–$C_6$-alkyl, $C_3$–$C_6$-alkenyl, $C_3$–$C_6$-alkinyl, $C_1$–$C_6$-alkoxy, $C_3$–$C_6$ -alkenyloxy, $C_1$–$C_4$-alkoxy-carbonyl-$C_1$–$C_2$-alkoxy, $C_1$–$C_6$-alkylamino, di-($C_1$–$C_2$-alkyl)-amino, $C_1$–$C_6$-alkylcarbonylamino, $C_1$–$C_6$-alkoxy-carbonylamino and $C_1$–$C_6$ alkylsulphonylamino, or a radical (optionally substituted by at least one of nitro, amino, cyano, carboxyl, halogen, $C_1$–$C_4$-alkyl, $C_1$–$C_2$-halogenoalkyl, $C_1$–$C_4$-alkoxy, $C_2$–$C_2$ -halogenoalkoxy, $C_1$–$C_4$alkylthio, $C_1$–$C_2$-halogenoalkylthio, $C_1$–$C_4$-alkoxy-carbonyl and di-($C_1$–$C_2$-alkyl)-amino selected from the group consisting of phenyl, phenyl-$C_1$–$C_4$-alkyl, phenoxy, phenyl-$C_1$–$C_4$-alkoxy, phenylamino, phenyl-$C_1$–$C_4$-alkyl-amino, N-($C_1$–$C_4$-alkyl)-N-phenylamino, pyridylamino, pyrimidylamino, pyridylcarbonylamino, phenylcarbonylamino, furylcarbonylamino, thienylcarbonylamino and phenylsulphonylamino, $R^{12}$ is hydrogen, cyano, carboxyl, $C_1$–$C_6$-alkoxycarbonyl, $C_1$–$C_6$-alkoxycarbonyl, $C_1$–$C_6$-alkylcarbonylamino or di- ($C_1$–$C_4$-alkoxy)-phosphoryl and $R^{13}$ is formyl, cyano, carboxyl, hydroxymethyl, carbamoyl or a radical (optionally substituted by halogen, carboxyl or $C_1$–$C_4$-alkoxycarbonyl) selected from the group consisting of $C_1$–$C_6$-alkoxycarbonyl, $C_5$–$C_6$-cycloalkyloxycarbonyl, $C_1$–$C_6$-alkylthio-carbonyl, $C_1$–$C_6$-alkylaminocarbonyl, $C_5$–$C_6$-cycloalkylamino-carbonyl, di-($C_1$–$C_2$- alkyl)-aminocarbonyl, $C_1$-$C_4$-alkylaminocarbonyl-$C_1$-$C_4$-alkoxycarbonyl, di- ($C_1$-$C_2$-alkyl)-aminocarbonyl-$C_1$-$C_2$-alkoxycarbonyl, phenylaminocarbonyl-$C_1$-$C_4$-alkoxycarbonyl and N-methyl-N-phenylaminocarbonyl-$C_1$-$C_4$-alkoxycarbonyl, or is a radical (optionally substituted by at least one of methyl and ethyl) selected from the group consisting of pyrrolidinylcarbonyl, piperidinylcarbonyl, morpholinylcarbonyl and piperazinylcarbonyl, or is a radical (optionally substituted by at least one of nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkoxy-carbonyl and di-($C_1$-$C_2$-alkyl)-amino) selected from the group consisting of phenoxycarbonyl, phenyl-$C_1$-$C_4$-alkoxycarbonyl, furylmethoxycarbonyl, thienylmethoxycarbonyl, phenylthiocarbonyl, phenyl-$C_1$-$C_4$-alkylthiocarbonyl, phenylaminocarbonyl, phenyl-$C_1$-$C_4$-alkylaminocarbonyl, N-($C_1$-$C_4$-alkyl)-N-phenylaminocarbonyl, phenylhydrazinocarbonyl, $C_1$-$C_4$-alkylhydrazinocarbonyl and phthalimidoxycarbonyl, or $R^{12}$ together with $R^{13}$ is —CO—O—$(CH_2)_n$—, where n is from 1 to 4, $R^{14}$ is hydrogen, fluorine, chlorine, methyl or methoxy, and Y is oxygen, sulphur, imino (NH) or methylimino ($NCH_3$), or a salt thereof.

2. A compound or salt according to claim 1, in which is hydrogen, hydroxyl, amino or a radical (optionally substituted by fluorine, chlorine, methoxy or ethyoxy) selected from the group consisting of methyl, ethyl, propyl, isopropyl, methoxy, ethoxy, propoxy, isopropoxy, cyanomethoxy, allyloxy, propargyloxy, methylthio-ethoxy, (nitro)-quinolyl-oxy, (fluoro)-phenylthio, (dimethoxy)-pyrimidinylthio, methylamino, ethylamino, propylamino, isopropylamino, dimethylamino, diethylamino, methoxycarbonyl-methylamino, methoxycarbonylethylamino, (chloro)-phenylethylamino, benzylamino, methylsulphonylamino, ethylsulphonylamino, phenylsulphonylamino and (dimethyl)hydrazino, $R^2$ is hydrogen, fluorine, chlorine, bromine, methyl, ethyl, propyl, isopropyl, phenyl, methoxy-carbonyl or ethoxycarbonyl, $R^3$ is hydrogen, methyl, ethyl, propyl or - if $R^2$ is hydrogen, alkyl or halogen - also may be fluorine, chlorine or bromine, $R^4$ is hydrogen, fluorine, chlorine, bromine, methyl, ethyl, propyl, isopropyl or phenyl, $R^5$ is hydrogen, methyl, ethyl, propyl, isopropyl or phenyl, $R^6$ is hydrogen, chlorine, fluorine, methyl, ethyl, methoxy, ethoxy, phenyl, methoxycarbonyl or ethoxycarbonyl, $R^7$ is hydrogen, methyl or ethyl or - if $R^6$ is hydrogen, alkyl or halogen - also may be chlorine or fluorine, $R^8$ is hydrogen, cyano, methyl, ethyl, phenyl, methoxycarbonylmethyl or ethoxycarbonylmethyl, $R^9$ and $R^{10}$ each independently is hydrogen, chlorine, methyl, ethyl, trifluoromethyl, methoxymethyl, methoxy, ethoxy, difluoromethoxy, methylthio, methylamino, ethylamino, dimethylamino, phenyl or phenoxy, X is oxygen or sulphur or - if $R^1$ is hydrogen or alkyl - also may be

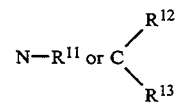

where $R^{11}$ is hydrogen, hydroxyl, amino, methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylamino, ethyoxycarbonylamino, methylsulphonylamino or ethylsulphonylamino, or is phenyl, benzyl, phenoxy, benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each optionally substituted by nitro, cyano, fluorine, chlorine, bromine, methyl, trifluoromethyl, methoxy, trifluoromethoxy, methylthio or trifluoromethylthio, $R^{12}$ is hydrogen, fluorine, chlorine, cyano, carboxyl, $C_1$-$C_4$-alkoxycarbonyl, $C_1$-$C_4$-alkylcarbonylamino, dimethoxyphosphoryl or diethoxyphosphoryl, and $R^{13}$ is formyl, cyano, carboxyl, hydroxymethyl, carbamoyl, or a radical (optionally substituted by fluorine, chlorine, carboxyl or $C_1$-$C_4$-alkoxycarbonyl) selected from the group consisting of $C_1$-$C_4$-alkoxycarbonyl, $C_5$-$C_6$-cycloalkyloxycarbonyl, $C_1$-$C_4$-alkylthiocarbonyl, $C_1$-$C_4$-alkylaminocarbonyl, $C_5$-$C_6$-cycloalkylaminocarbonyl, dimethylaminocarbonyl, $C_1$-$C_4$-alkylaminocarbonyl-$C_1$-$C_4$-alkoxycarbonyl, dimethylaminocarbonyl-$C_1$-$C_4$-alkoxycarbonyl and N-methyl-N-phenylaminocarbonyl-$C_1$-$C_4$-alkoxycarbonyl, or a radical (optionally substituted by at least one of methyl and ethyl) selected from the group consisting of pyrrolidinylcarbonyl, piperidinylcarbonyl, morpholinylcarbonyl and piperazinylcarbonyl or is a radical (optionally substituted by nitro, cyano, fluorine, chlorine, bromine, methyl, trifluoromethyl, methoxy, trifluoromethoxy, methylthio or trifluoromethylthio) selected from the group consisting of phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl, phenylhydrazinocarbonyl and phthalimidoxycarbonyl, or $R^{12}$ together with $R^{13}$, is

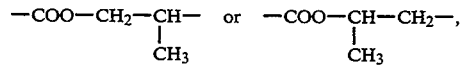

$R^{14}$ is hydrogen, and
Y is oxygen or imino (NH).

3. A compound or salt according to claim 1, in which

R¹ is hydroxyl, methoxy, ethoxy, propoxy, propargyloxy, cyanomethoxy, methylthioethoxy, methoxycarbonylmethylamino, methoxycarbonylethylamino, 4-chlorophenylethylamino, methylsulphonylamino, phenylsulphonylamino or 2,2-dimethylhydrazino, R² is hydrogen, fluorine, chlorine, methyl or ethyl,
R³ is hydrogen, methyl or ethyl,
R⁴ is hydrogen, methyl, ethyl, propyl or isopropyl,
R⁵ is hydrogen, methyl or ethyl,
R⁶ is hydrogen, methyl or ethyl,
R⁷ is hydrogen, methyl or ethyl,
R⁸ is hydrogen or methyl,
R⁹ is hydrogen, methyl or methoxy,
R¹⁰ is methyl or methoxy,
X is oxygen,
R¹⁴ is hydrogen, and
Y is oxygen.

4. A compound according to claim 1, wherein such compound is 2-(4,6-dimethoxy-pyrimidin-2-yloxy)-5-methyl-bicyclo-[3.1.0]hexane-1-carboxylic acid of the formula

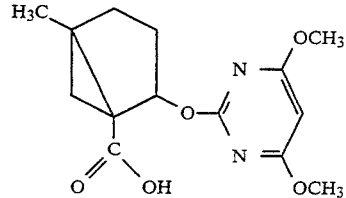

or a salt thereof.

5. A herbicidal composition comprising a herbicidally effective amount of a compound or salt thereof according to claim 1 and a diluent.

6. A method of combating unwanted vegetation which comprises applying to such vegetation or to a locus from which it is desired to exclude such vegetation a herbicidally effective amount of a compound or salt thereof according to claim 1.

7. A method of combating unwanted vegetation which comprises applying to such vegetation or to a locus from which it is desired to exclude such vegetation a herbicidally effective amount of a compound or salt thereof according to claim 4.

* * * * *

UNITED STATES PATENT AND TRADEMARK OFFICE
CERTIFICATE OF CORRECTION

PATENT NO. : 5,439,874
DATED : August 8, 1995
INVENTOR(S) : Drewes, et al.

It is certified that error appears in the above-indentified patent and that said Letters Patent is hereby corrected as shown below:

| | |
|---|---|
| Col. 3, line 55 | Delete " $C_3-C_{b6}$-alkenyl " and substitute -- $C_3-C_6$-alkenyl -- |
| Col. 26, line 16 | Delete " $'R^5$ " |
| Col. 26, line 17 | Before " is " insert -- $R^5$ -- |
| Col. 26, line 50 | Delete " $C_2-C_2$-halogenoalkoxy " and substitute -- $C_1-C_2$-halogenoalkoxy --, after " $C_4$ " insert -- - -- |
| Col. 26, line 52 | After " -amino " insert -- ) -- |
| Col. 26, line 59 | After " hydrogen " insert -- halogen -- |
| Col. 26, line 60 | Delete " $C_1-C_6$-alkoxycarbonyl " |
| Col. 27, line 3 | Delete " $C_1-C_2$-alkoxycarbonyl " and substitute -- $C_1-C_4$-alkoxycarbonyl -- |
| Col. 27, line 32 | Before " is " insert -- $R^1$ -- |

UNITED STATES PATENT AND TRADEMARK OFFICE
CERTIFICATE OF CORRECTION

PATENT NO. : 5,439,874
DATED : August 8, 1995
INVENTOR(S) : Drewes, et al.

It is certified that error appears in the above-indentified patent and that said Letters Patent is hereby corrected as shown below:

Col. 27, line 33   Delete " ethyoxy " and substitute -- ethoxy --

Signed and Sealed this

Twelfth Day of December, 1995

Attest:

BRUCE LEHMAN

Attesting Officer

Commissioner of Patents and Trademarks